Figure 1:
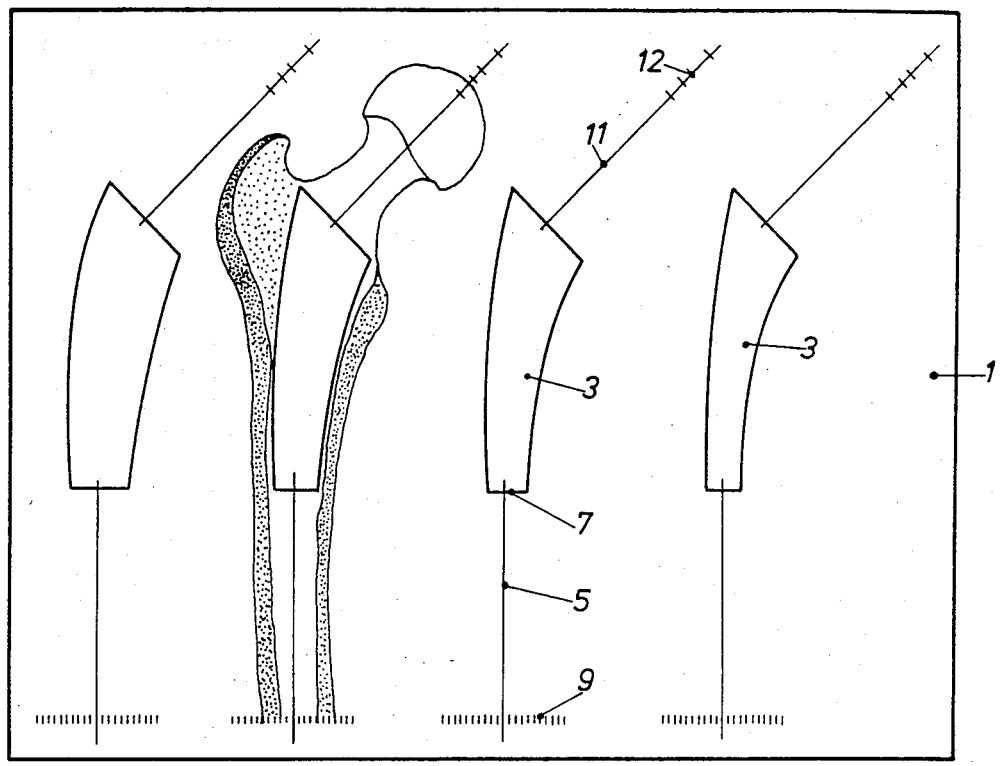

United States Patent [19]

Link

[11] Patent Number: 4,658,808
[45] Date of Patent: Apr. 21, 1987

[54] ARRANGEMENT FOR PREPARING AN ANATOMICALLY MEASURED ENDOPROSTHESIS

[75] Inventor: Helmut D. Link, Hamburg, Fed. Rep. of Germany

[73] Assignee: Waldemar Link GmbH & Co., Hamburg, Fed. Rep. of Germany

[21] Appl. No.: 729,379

[22] Filed: May 1, 1985

[30] Foreign Application Priority Data

May 11, 1984 [DE] Fed. Rep. of Germany ....... 3417609

[51] Int. Cl.$^4$ .............................................. A61F 2/30
[52] U.S. Cl. ..................................... 623/16; 128/774; 33/511; 33/512
[58] Field of Search .................... 378/62; 33/511, 512, 33/562, 563; 128/92 C, 92 CA, 92 G, 303 R; 623/16, 22, 23

[56] References Cited

U.S. PATENT DOCUMENTS 4,135,517  1/1979  Reale .............................. 128/303 R
4,141,088  2/1979  Treace et al. ..................... 128/92 C
4,578,081  3/1986  Harder et al. ......................... 623/22

OTHER PUBLICATIONS

"Restoration of Rheumatoid Finger-Joint Function" by Adrian E. Flatt, M.D., *The Journal of Bone and Joint Surgery* vol. 45A, No. 5, Jul. 1963, pp. 1101–1103.

*Primary Examiner*—Kyle L. Howell
*Assistant Examiner*—Randy Citrin
*Attorney, Agent, or Firm*—Townsend and Townsend

[57] ABSTRACT

An arrangement for preparing an anatomically measured endoprosthesis with a stem to be anchored in the widening end of a hollow bone, in particular a hip joint stem prosthesis to be anchored in the femur, uses radiographs true to scale, a set of a limited number of prosthesis templates and a set of corresponding prosthesis preparation models. In order to obtain greater variability and facilities for individual adaptation, a set of partial templates for that part of the prosthesis stem is provided which is to be anchored in the outer bone section forming the greatest widening. To determine the dimensions of the adjoining prosthesis stem sections, a direction scale and indicator are provided, the partial template and the a direction scale and indicator being mutually connected or connectable in defined directions. A set, corresponding to the partial templates, of trial preparation sections which are connectable to trial prosthesis sections; and for the adjoining prosthesis sections, is provided. Advantageously, the a direction indicator and scale are also each formed by one set of partial templates.

11 Claims, 9 Drawing Figures

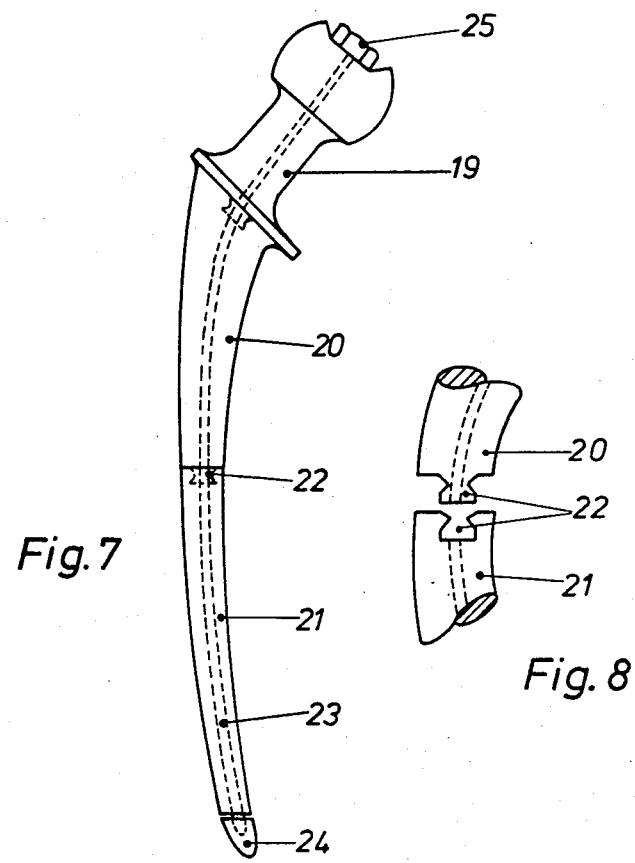
Fig. 7
Fig. 8
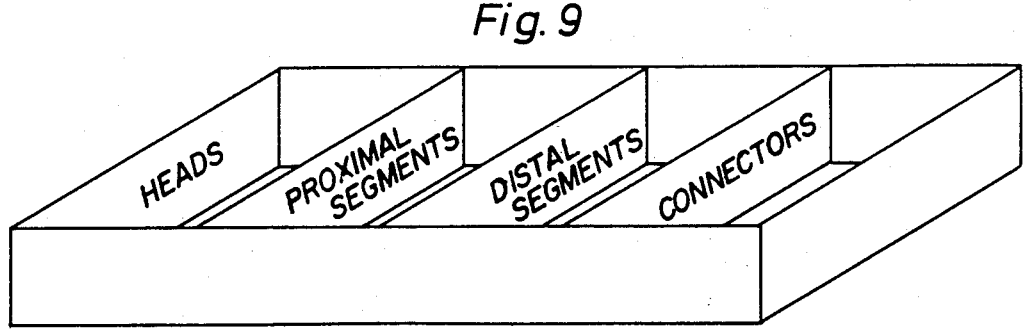
Fig. 9

ARRANGEMENT FOR PREPARING AN ANATOMICALLY MEASURED ENDOPROSTHESIS

DESCRIPTION

The invention relates to an arrangement for preparing an anatomically measured endoprosthesis with a stem to be anchored in the widening end of a hollow bone, in particular a joint stem prosthesis to be anchored in the femur, using radiographs true to scale, a set of a limited number of prosthesis templates and a set of corresponding prosthesis preparation models.

It is known that an endoprosthesis for a particular patient can be selected in a measured form by comparing templates reproducing the shape of the prosthesis in the AP and LM planes with true-to-scale radiographs in the AP and LM planes by superposition. Naturally, however, the individual adaptation possibilities are limited, if models and templates of only a restricted number of complete prostheses are available. This known method can no longer satisfy the increasing trend towards individual adaptation, in particular also under the aspect of cement-free anchoring.

It is known (European Published Application No. 93,869) to prepare individually adapted endoprostheses by making a complete spatial image of the bone, to be fitted with the endoprosthesis, by computed tomography or a comparable technique and by deriving the appropriate shape of the endoprosthesis from this with computer assistance. This method, however, is very expensive and can be carried out only in conjunction with unusually well equipped hospitals.

It is therefore the object of the invention to provide an arrangement of the type described at the outset, which allows the preparation of anatomically measured prostheses in a simpler manner.

The object is achieved according to the invention when a set of partial templates for that part of the prosthesis stem which is to be anchored in the outer bone section forming the greatest widening and dimensioning means for determining essential dimensions of the adjoining sections of the bone and the prosthesis sections to be fitted therein are provided, the partial templates and the dimensioning means being mutually connected or connectable in defined directions, and when a set, corresponding to the partial templates, of preparation models, which are connectable to preparation models for the adjoining prosthesis sections, is provided.

The starting point of the invention is the experience that certain sections of the bone part receiving the prosthesis stem always have characteristic variations in their form, these variations in one section being largely independent of those in the other section. The greatest differences in form occur in that end section of the bone which forms the greatest widening, namely in the case of a femur approximately in the region above the lower boundary line of the lesser trochanter. The invention also exploits the discovery that it is quite unnecessary to aim for an individual adaptability in infinite fineness, but rather that a graduation is justifiable in view of the inaccuracies which are unavoidable anyway or can be tolerated The invention essentially comprises the recognition that the number of models and of the templates associated with them can be kept relatively small, provided that the particular, anatomically most appropriate dimensions and forms are separately determined in the individual, characteristic bone regions.

The means, connected to the template, for determining the dimensions of the adjoining prosthesis parts are advantageously likewise each formed by one set of partial templates which, as subsidiary partial templates, supplement the abovementioned main partial templates. This makes it possible to fix the shape of a prosthesis by assembling template sections of different shapes. The templates are here used not only for fixing the diameter and length dimensions of the prosthesis sections under consideration, but they must also give an indication of their direction in relation to the direction of the main template. For this reason, they ought to be connectable to the main partial template in defined directions, that is to say it must be possible to relate their direction to a predetermined reference direction of the main main partial template. This definition of directions is most easily accomplished when the main partial templates and the subsidiary partial templates are mutually connected or connectable in fixed directions by interacting guide means. However, this is not absolutely necessary. For example, they can be pivotably joined at the boundary point, and the particular selected angle can be expressed by the angle of the longitudinal direction of the subsidiary partial template relative to a reference direction fixed by the main partial template. However, the interaction of the templates in fixed directions by guide means is to be preferred, if only because errors in the determination of the prosthesis form can be excluded with greater certainty.

In the simplest case, the interacting guide means of the partial templates are straight edges, along which the templates can be laid side by side. An embodiment, in which the sets of partial templates are arranged on carrier strips which are displaceable parallel to one another, is especially advantageous and simple. When laid side by side, the extended longitudinal edges of these carrier strips form secure guide edges. It is also possible to arrange the partial templates or sets of partial templates in an apparatus which is fitted with appropriate mechanical guide means and which, advantageously, also forms a holder for the respective radiograph.

In the case of a hip joint/femur stem prosthesis, the partial template associated with the proximal stem section advantageously has a mean length of about 8 cm, measured from the proximal end of the stem up to its distal end forming the boundary towards the next template. It is also advantageous when the distal end of this partial template, that is to say the boundary towards the next section of the prosthesis stem, is located in the transition region from the proximal curvature, with the centre of curvature located at the front, to the distally adjacent curvature with the centre of curvature located at the back. On the one hand, it has been found that the proximal part, in which the greatest individual differences in dimensions occur, is particularly well outlined by this boundary. On the other hand, optimum adaptation in the case of different curvature conditions of the bone can be found in this way. In general, two sets of templates associated with the prosthesis stem then suffice for an appropriate definition of a hip joint prosthesis stem.

As soon as the templates have been selected such that they fit the radiographs, the prosthesis which individually and exactly fits the bone within the envisaged tolerances can then be developed from this, by assembling the preparation models associated with the templates and using them for casting a corresponding prosthesis.

In order to give the surgeon an idea of the appearance of the prosthesis assembled by him, sets of trial prosthesis sections, which correspond to the templates and preparation models and are fitted with devices for interlocking assembly, can be provided. With these, the surgeon can then assemble a trial prosthesis corresponding to the templates which he regards as the correct ones, and can convince himself of the correctness of his choice by the three-dimensional inspection.

Figure 2:
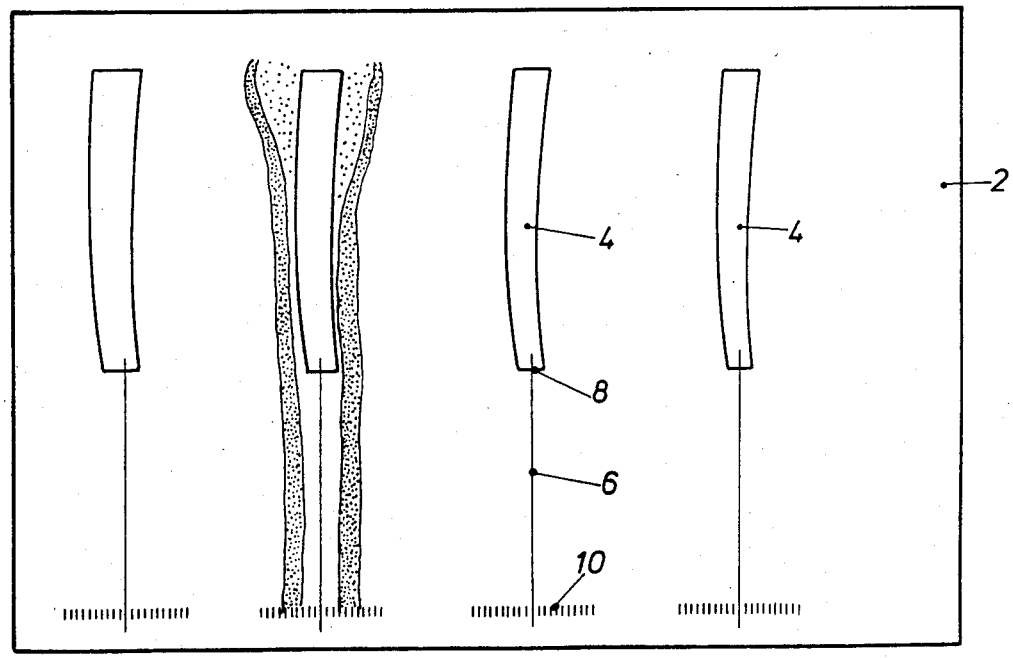
Figures 3, 4:
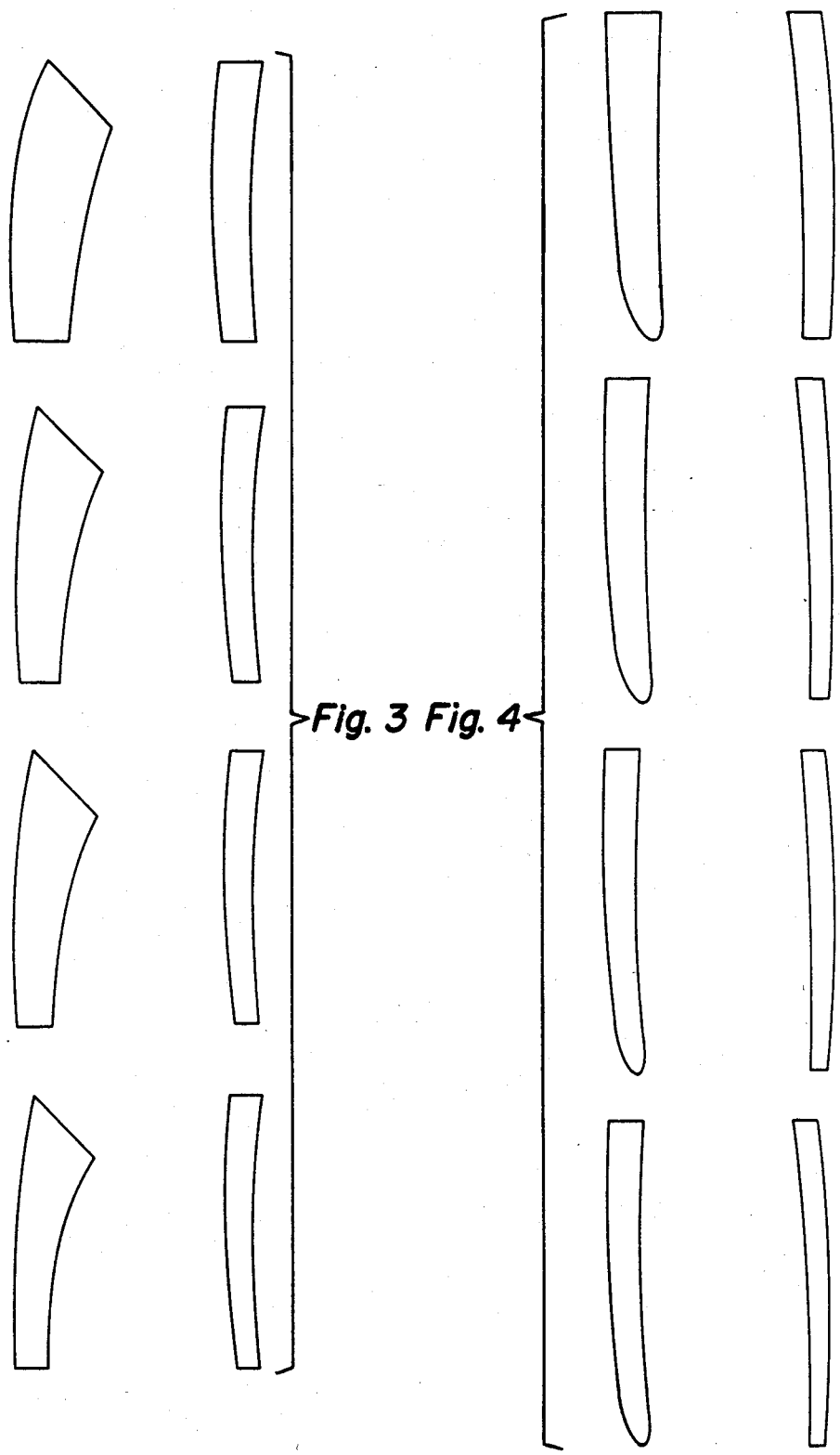
Figure 5:
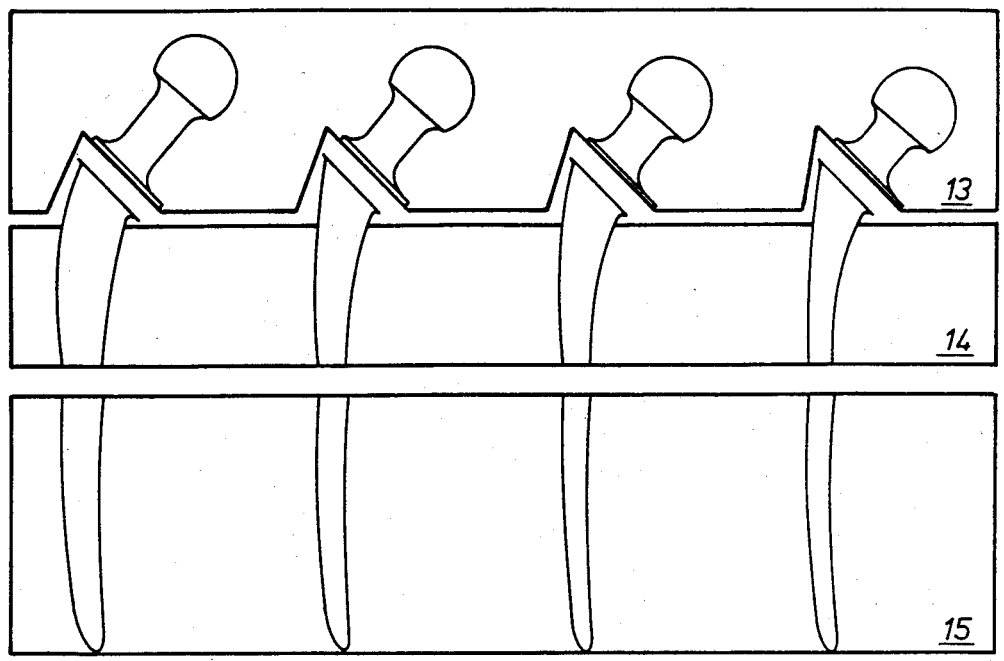
Figure 6:
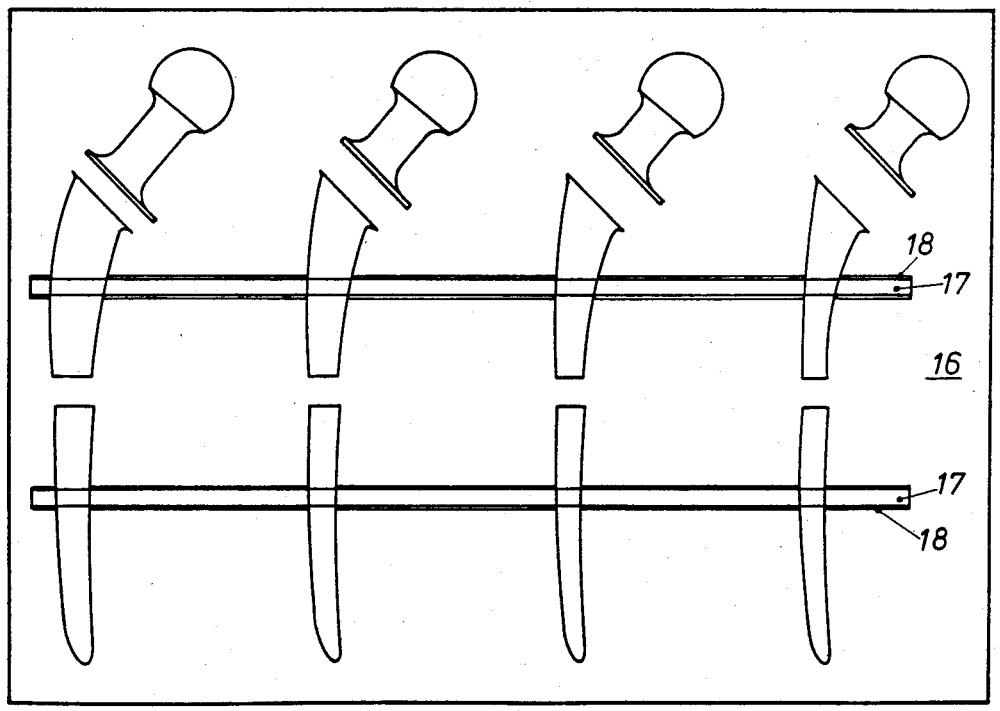

The invention is explained in more detail below by reference to the drawing which represents advantageous illustrative embodiments and in which:

FIG. 1 shows a first embodiment of a template sheet with different partial templates in the LM plane, FIG. 2 shows a template sheet, associated with the template sheet according to FIG. 1, in the AP plane, FIG. 3 shows, in the left-hand vertical row, a set of templates of the proximal femur stem sections in the LM plane and, in the right-hand vertical row, in the AP plane, FIG. 4 shows two sets, corresponding to and associated with FIG. 3, of the distal femur stem sections, FIG. 5 shows a template sheet, consisting of three strips, for a hip joint femur stem prosthesis in a representation in the LM plane, FIG. 6 shows a template sheet, similar to FIG. 5, with partial templates displaceable on guides, FIG. 7 shows a trial prosthesis, FIG. 8 shows the connection arrangements between two parts of the trial prosthesis and FIG. 9 shows a parts box for trial prostheses.

On the template sheets 1 and 2 according to FIGS. 1 and 2, a set of partial templates of the proximal section of the stem of a hip joint stem prosthesis can be seen in the LM and AP planes respectively. The thicknesses and curvatures of these prosthesis sections have a graduation which represents all conditions, occurring in practice, with sufficient fineness. Of course, a larger number of variations than the four shown can be provided. The sheets are transparent, so that their representations can be brought into congruence with true-to-scale radiographs, as indicated in FIGS. 1 and 2 each time for the second partial templates from the left. The surgeon can thus select the partial template fitting the particular case. Each partial template 3 or 4 is connected to a direction indicator 5 or 6 respectively, which points to the distal end and has a lateral line scale 9 or 10 at a few centimetres distance from the lower end edge 7 or 8. This line scale is located at a point characteristic of the thickness of the distal prosthesis stem section, for example in the region between its centre and its distal end. The reading on this line scale allows fixing of both the thickness and the direction of the distal prosthesis stem section. If, for example, the distal stem section on the second template from the left in FIG. 1 is characterised by "two lines left, four lines right", this fixes both the thickness of the stem in this imaging plane at six lines and the direction at one line right.—In addition, a direction indicator 11 with a line scale 12 for fixing the head/neck length is connected to the template 3.

The prosthesis manufacturer has a set of prefabricated casting models available for the proximal stem section which is represented by the partial templates 3 or 4, as well as sets of casting models for the adjoining prosthesis sections which are selected in accordance with the thickness and direction data and are connected to the main partial models for forming the complete casting model.

Instead of identifying the dimensions and directions of the sections adjoining the main partial section of the prosthesis only by numbers in accordance with FIGS. 1 and 2, partial templates can also be provided for this purpose. FIG. 3 shows a set of main partial templates for the proximal section of a femur stem prosthesis in the LM representation (on the left) and the AP representation (on the right). These representations correspond to those in FIGS. 1 and 2. Corresponding representations of a set of subsidiary partial templates for the distal stem section are shown in FIG. 4 (LM plane on the left, AP plane on the right). It will be seen that the complete form of the stem can be remodelled by assembling in each case one main and one subsidiary partial template in the particular representation plane. The mutual alignment of the templates is obtained by laying their straight boundary edges against one another without a gap. The prosthesis manufacturer again has a corresponding set of casting models available, and any diameter differences in the boundary region can be compensated. In the representations in the AP plane, shown on the right in each of FIGS. 3 and 4, it will be seen that the proximal section (FIG. 3) has a curvature with the centre of curvature located at the front, and the lower section has a curvature with the centre of curvature located at the back, and that the boundary between the two partial templates or models is located in the region of the point of inflection of the curvature. In humans, this point always lies in the range from about 4 cm to 11 cm below the trochanter major top edge/trochanter minor top edge plane. Any curvature changes in this region are immaterial in practice, because the marrow cavity runs here approximately straight.

Since the use of individual partial templates, as shown in FIGS. 3 and 4, is involved, FIG. 5 envisages an assembly of partial templates associated with the same section on a template strip in each case. The template strip 13 shows the head/neck portion in different lengths. The strip 14 contains the partial templates for the upper stem region, and section 15 shows the partial templates for the lower stem section. Since these strips have extended straight boundary edges, good mutual guidance is obtained when used in practice, so that angle errors on assembly of the individual templates are virtually excluded. Obviously, the template according to FIG. 5, which contains the representations in the LM plane, is associated with a corresponding template for the representations in the AP plane, which was not shown for the sake of simplicity.

An arrangement similar to that of FIG. 5 is shown in FIG. 6. The head/neck portions are shown fixed on the template sheet 16, whereas the partial templates for the stem are fastened to plastic rails 17 which in turn are displaceable in corresponding guides 18 on the template sheet 16.

The trial prosthesis according to FIG. 7 is composed of sections 19, 20 and 21 which, as illustrated in FIG. 8 in an approximately full-sized representation, are fitted with dovetail connecting profiles 22, by means of which they can be assembled in fixed directions. In order to prevent sliding apart, the sections are drilled through in the longitudinal direction and are held together by a flexible tension element 23 which is firmly connected at one end to the tip 24 of the prosthesis stem and can be tensioned at the other end by a nut 25.

For the assembly of such trial prostheses, sets of prosthesis sections each corresponding to the partial templates are provided and assembled in a container, for example of the form shown in FIG. 9.

I claim:

1. A kit for making a customfit prosthetic implant including a stem to be anchored in a bone canal of a patient, the kit comprising:
   first and second template sets, each set including a plurality of templates, the sets of templates corresponding to longitudinally adjacent sections of the implant, each template in each set having a defined periphery which corresponds to a possible longitudinal cross-sectional shape of the bone canal;
   first and second sets of trial prosthesis sections, each section being configured to correspond to the shape of a template in the first and second template sets; and
   means carried by the trial prosthesis sections so that any section of the first set can be joined to any section of the second set end-to-end to define a core of a particular shape from which the prosthetic implant can be cast;
   whereby the customfit prosthesis can be made by providing a radiograph of the bone into which the implant is to be implanted, determining which templates from the first and second template sets correspond in shape to the shape of the bone canal on the radiograph, and thereafter generating the core from which the implant is to be made by connecting end-to-end the trial prosthesis sections which correspond to the selected templates.

2. A kit as in claim 1 further comprising means for measuring sections of a bone adjoining a template when the template is superimposed on a radiograph of a femur.

3. A kit as in claim 2 wherein the first template set comprises a plurality of templates having the form of a proximal section of a femur implant and wherein the measuring means is integrally formed with each template.

4. A kit as in claim 2 wherein the first template set comprises a plurality of templates having the form of a distal section of a femur implant and wherein the measuring means is integrally formed with each template.

5. A kit as in claim 4 wherein each proximal section template has a mean length of about 8 cm.

6. A kit as in claim 4 wherein the proximal and distal section templates, when matched together in an anterior-posterior plane, form a curve, and wherein the meeting point of the templates occurs in the region of a point of inflection.

7. A kit as in claim 1 further comprising:
   a guide having a plurality of templates disposed thereon in a prescribed orientation.

8. A kit as in claim 7 wherein the guide comprises a carrier strip slidingly disposed within a channel, the plurality of templates being disposed on the carrier strip in a prescribed orientation.

9. A kit as in claim 1 wherein a plurality of templates are mutually connected.

10. A kit for preparing an anatomically measured hip joint prosthesis having a stem anchored in the widening end of a femur comprising:
    a plurality of templates having the form of a proximal section of a hip joint prosthesis in a lateral-medial plane;
    a plurality of templates having the form of a proximal section of a hip joint prosthesis in an anterior-posterior plane;
    a plurality of templates having the form of a distal section of a hip joint prosthesis in a lateral-medial plane; and
    a plurality of templates corresponding to a distal section of a hip joint prosthesis in an anterior-posterior plane;
    a trail prosthesis section associated with each template;
    means for coupling the trial prosthesis section to an adjoining trial prosthesis section.

11. A kit as in claim 2 wherein the measuring means comprises a direction indicator having opposite ends and a scale for measuring sections of a bone adjoining a template when the template is superimposed on a radiograph of a femur, one end of the direction indicator being connected to the template and extending therefrom in a prescribed orientation, and the other end of the directIon indiator being connected to the scale.

* * * * *